United States Patent [19]

Zimmer et al.

[11] Patent Number: 4,994,481
[45] Date of Patent: Feb. 19, 1991

[54] TREATMENT OF AIDS WITH DIPHENYLHYDANTOIN AND ITS DERIVATIVES

[76] Inventors: Pascal Zimmer, Lehrertalweg 112; Hans A. Lehr, Werastrasse 15, both of D-7900 Ulm, Fed. Rep. of Germany

[21] Appl. No.: 22,671

[22] Filed: Mar. 6, 1987

[30] Foreign Application Priority Data

Mar. 6, 1986 [DE] Fed. Rep. of Germany ....... 3607381

[51] Int. Cl.$^5$ .......................................... A61K 31/415
[52] U.S. Cl. ..................................................... 514/391
[58] Field of Search ......................................... 514/391

[56] References Cited

U.S. PATENT DOCUMENTS 4,163,058  7/1979  Stella et al. .......................... 514/319

Primary Examiner—Jerome D. Goldberg
Attorney, Agent, or Firm—Steinberg & Raskin

[57] ABSTRACT

The invention relates to a method of use of diphenylhydantoin and its derivatives for the treatment of AIDS. The invention further relates to a pharmaceutical composition which is useful for such treatment.

The compounds which are used according to the invention exert a specific masking effect on specific receptors of the lymphocytes and are thus in a position to prevent a virus attack on the lymphocytes.

4 Claims, No Drawings

TREATMENT OF AIDS WITH DIPHENYLHYDANTOIN AND ITS DERIVATIVES

The invention relates to a method of use of diphenylhydantoin and its derivatives in the treatment of AIDS. The invention further relates to a pharmaceutical composition comprising an effective amount of diphenylhydantoin and its derivatives.

Since 1938 diphenylhydantoin (DPH) has been used as an anticonvulsive agent. The systemic action of DPH and its effect on the central nervous system are well known. Further, DPH has an antiarrhythmic effect.

It is an object of the invention to provide an effective treatment of immune diseases. These and other objects will be apparent from the description and the claims.

It has now been surprisingly found that DPH has a specific influence on the T-lymphocytes and is therefore useful for the treatment of AIDS.

The invention thus relates to a method of use of diphenylhydantoin and its derivatives of general formula (I)

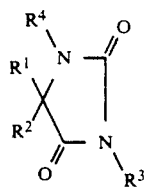

wherein $R^1$ und $R^2$, which can be the same or different, each designate a hydrogen atom, a phenyl radical, which can be substituted by a halogen atom, a hydroxy group, a $C_1$-$C_4$-alkoxy group or a $C_1$-$C_4$-alkyl group, a $C_1$-$C_4$-alkyl group, which can be substituted by a hydroxy group or a $C_1$-$C_4$-alkoxy group, a $C_5$-$C_6$-cycloalkyl group or a thiophene group, and wherein $R^3$ and $R^4$, wich can be the same or different, each designate a hydrogen atom, a $C_1$-$C_4$-alkoxy group, $C_1$-$C_4$-alkyl group or phenyl group, and the pharmaceutically acceptable salts thereof, in the treatment of AIDS.

Preferably, $R^1$ and $R^2$ designate an optionally substituted phenyl- or $C_1$-$C_4$-alkyl radical, for example p-hydroxyphenyl, p-tolyl, methyl, ethyl, n- and i-propyl, n-butyl or t-butyl.

$R^4$ and $R^5$ preferably designate a hydrogen atom or a $C_1$-$C_4$-alkyl group.

Particularly preferred for the treatment of AIDS is the diphenylhydantoin of the formula

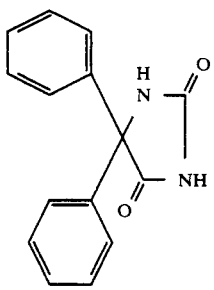

and the compounds of the formulae

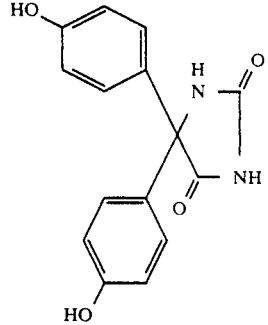

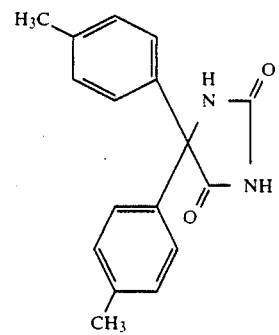

The invention further relates to a method of treatment of AIDS.

The invention further relates to a pharmaceutical composition, comprising an effective amount of diphenylhydantoin and its derivatives of the general formula (I):

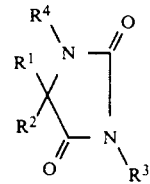

wherein $R^1$ und $R^2$, which can be the same or different, each designate a hydrogen atom, n phenyl radical, which can be substituted by a halogen atom, a hydroxy group, a $C_1$-$C_4$-alkoxy group or a $C_1$-$C_4$-alkyl group, a $C_1$-$C_4$-alkyl group, which can be substituted by a hydroxy group or a $C_1$-$C_4$-alkoxy group, a $C_5$-$C_6$-cycloalkyl group or a thiophene group, and wherein $R^3$ and $R^4$, which can be the same or different, each designate a hydrogen atom, a $C_1$-$C_4$-alkoxy group, $C_1$-$C_4$-alkyl group or phenyl group, and the pharmaceutically acceptable salts thereof.

As mentioned, the compounds used in accordance with the invention serve to treat immune diseases, in particular diseases which are mediated by T-lymphocytes. The compounds according to the invention are particularly suited for the treatment of AIDS (Acquired Immune Deficiency Syndrome).

On the basis of tests which are explained in detail below, it was found that the compounds used according to the invention bind lymphoeticular cells to the membrane and exert a specific masking effect on the receptors of viruses of the type HTLV-III/LAV. In this context it is essential that the other functions of the lymphocytes which they possess within the frame of their immune response are not adversely affected.

The following tests confirm this fact:

1. Marking of lymphocyte membrane with immunofluorescent viruses of type HTLV-III/LAV (a) From 4 patients, who had been treated at least 10 days with therapeutically doses of diphenylhydantoin (3×100 mg epanutine p.o./day), each 15 ml blood were taken which after adding with sodium citrate (2 ml/15 ml blood) were stored for 48 hours.

The lymphocytes were isolated using the known Ficoll/Hypaque layer technique. 1 million viable lymphocytes were incubated thereafter for 1 hour at 4° C. together with 50 ml immunofluorescent HTLV-III/-LAV, corresponding to 8000 ng of the virus. After twice 10 minutes wash in phosphate buffer solution the cells were diluted with a mixture of phosphate buffer solution/glycerol of the same concentrations. The immunofluorescent marking was thereafter determined using an immunofluorescent microscope.

(b) In similar manner the marking of the lymphocyte membrane with HTLV-III/LAV was performed by treating 15 ml each of heparinised blood of 4 further patients as explained under point (a) above. The blood was previously stabilized with heparin and stored for 5 hours.

(c) The T-lymphocytes were isolated as described above from patient blood which previously had not been treated with diphenylhydantoin. These T-lymphocytes were treated with diphenylhydantoin in concentrations of 2 μg/ml and 20 μg/ml, respectively, in RPMI 48 hours. Thereafter, the lymphocytes were isolated and incubated with immunofluorescent HTLV-III/LAV as described above. Thereafter, the immunofluorescence marking was performed with the aid of an immunofluorescence microscope.

Lymphocytes which had been isolated from patient blood which had not previously been treated with diphenylhydantoin were used as control. These lymphocytes were incubated as described above with immunofluorescent HTLV-III/LAV without having been treated with diphenylhydantoin and their immunofluorescence marking was evaluated.

The results are compiled on the following tables:

TABLE I

Results of Test 1a (Stabilization of Blood with Sodium Citrate)

| Patient[1] No. | membrane marking with immunofluorescent HTLV-III/LAV % | diffuse marking % |
|---|---|---|
| 1 | — | 2,2 |
| 2 | — | 2,3 |
| 3 | — | 1,0 |
| 4 | — | 1,8 |
| control | 8,2 | — |

TABLE II

Results of Test 1b (Stabilization of Blood with Heparin)

| Patient No. | membrane marking with immunofluorescent HTLV-III/LAV % | diffuse marking % |
|---|---|---|
| 5 | — | 2,4 |
| 6 | — | 2,6 |
| 7 | — | 1,3 |
| 8 | — | 3,0 |
| control | 8,2 | — |

TABLE III

| treatment of lymphocytes with | Results of Test 1c membrane marking with immunofluorescent HTLV-III/LAV % | diffuse marking % |
|---|---|---|
| 2 μg/ml DPH | 8.6 | 4 |
| 20 μg/ml DPH | 1,5 | 2,5 |
| control | 8,9 | 5 |

2. Lymphocytes which had been treated with DPH were thereafter marked with monoclonal antibodies (OKT 4,4 OKT 8, OKT 3, OKT 11) and the marking pattern was evaluated. The marking pattern did not differ from the pattern which is exhibited by untreated T-lymphocytes.

From tables I and II one can see that with lymphocytes which originate from patients treated with diphenyl-hydantoin or which had been treated with diphenyl-hydantoin in vitro, respectively, no immunofluorescence marking occurs. The T-lymphocytes thus treated merely show a slight diffuse marking.

Without being bound to any theory, this finding can be explained such that diphenylhydantoin binds to the membrane of lymphocytes and marks the receptors for HTLV-III/LAV so that the viruses are no longer in position to associate at the cell membrane or to perfuse them.

In contrast thereto, data for the untreated control samples show that the membrane of T-lymphocytes is marked by immunofluorescent HTLV-III/LAV and is thus attacked.

Test 2 verifies that that the diphenylhydantoin derivatives which are used according to the invention mask the receptors for viruses of the type HTLV-III/LAV specifically, that is an attack of HTLV-III/LAV cannot occur while the other functions of the lymphocytes are maintained in the frame of the immune response.

Additionally, the administration of the compounds used according to the invention has as a result that the lymphocytes newly formed in the bone marrow are influenced in the same manner prior to the differentiation into B- and T-lymphocytes and into specific T-cell subpopulations, respectively, particularly T-helper cells, in the same manner and are thus protected against a virus attack. This has as a result that in the organism a growing population of protected, healthy T-lymphocytes prevails which in the course of time replace the infected lymphocytes.

The diphenylhydantoin derivatives used according to the invention are thus particularly suited for the prophylactic, palliative and curative treatment of AIDS.

The compounds can be used alone or in combination with other, suitable active agents. Further, specific supportive therapies are possible, for example the implantation of bone marrow or thymus, doses of HLA-identical lymphocytes and doses of thymus hormon or extract.

The diphenylhydantoin derivatives can be administered orally or parenterally, preferably in the form of a salt, for example the sodium salt. Upon oral administration these compounds are confectioned in usual forms of application, for example as tablet, capsule, etc. together with conventional additives and auxiliary agents. For injection preparations these compounds are normally used as sodium salt and are dissolved in an appropriate solvent or a solvent mixture, for example water mixed with glycols or glycerol.

The dosage of the diphenylhydantoin derivatives is performed in accordance with type and severeness of the disease. A range of 10 to 1500 mg/per day, preferably 100 to 1000 mg/per day is considered useful. Generally, a dosage of 300 mg/per day is used.

FORMULATION EXAMPLES:

1. Capsule 100 mg of diphenylhydantoin are filled into a soft gelatine capsule and can be administered in this manner.

2. Infusion solution

12% diphenylhydantoin-sodium-salt
16% tetraglycol
11% trisbuffer
injection water up to 100%

3. Injection preparations diphenylhydantoin-sodium-salt 250 mg
tetraglycol solution up to 5 ml

What we claim is:

1. Method of treating the immune disease, AIDS, which comprises administering to a patient suffering from the same, an AIDS treatment effective amount of a diphenylhydantoin of the formula:

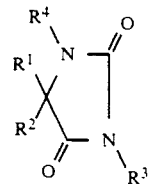

wherein $R^1$ and $R^2$ are each hydrogen, phenyl or phenyl substituted by halogen, hydroxyl, $C_1$-$C_4$ alkyl, $C_1$-$C_4$ hydroxyalkyl, $C_5$-$C_6$ cycloalkyl or thiophene, and wherein $R^3$ and $R^4$ are each hydrogen, $C_1$-$C_4$ alkoxy, $C_1$-$C_4$ alkyl or phenyl, and pharmaceutically acceptable salts thereof.

2. Method according to claim 1, wherein $R^1$ and $R^2$ are each phenyl and $R^3$ and $R^4$ are each hydrogren.

3. Method according to claim 1, wherein $R^1$ and $R^2$ are each hydroxyphenyl and $R^3$ and $R^4$ are each hydrogen.

4. Method according to claim 1, wherein $R^1$ and $R^2$ are each methylphenyl, and $R^3$ and $R^4$ are each hydrogen.

* * * * *